United States Patent [19]
Fraley et al.

[11] Patent Number: 5,858,742
[45] Date of Patent: *Jan. 12, 1999

[54] CHIMERIC GENES FOR TRANSFORMING PLANT CELLS USING VIRAL PROMOTERS

[75] Inventors: Robert Thomas Fraley; Robert Bruce Horsch, both of St. Louis; Stephen Gary Rogers, Chesterfield, all of Mo.

[73] Assignee: Monsanto Company, St. Louis, Mo.

[ * ] Notice: The term of this patent shall not extend beyond the expiration date of Pat. Nos. 5,530,196 and 5,352,605.

[21] Appl. No.: 669,672

[22] Filed: Jun. 24, 1996

Related U.S. Application Data

[63] Continuation of Ser. No. 300,029, Sep. 2, 1994, Pat. No. 5,530,196, which is a continuation of Ser. No. 146,621, Oct. 28, 1993, Pat. No. 5,352,605, which is a continuation of Ser. No. 625,637, Dec. 7, 1990, abandoned, which is a continuation of Ser. No. 931,492, Nov. 17, 1986, abandoned, which is a continuation-in-part of Ser. No. 485,568, Apr. 15, 1983, abandoned, which is a continuation-in-part of Ser. No. 458,414, Jan. 17, 1983, abandoned.

[51] Int. Cl.$^6$ .......................... C12N 15/34; C12N 15/54; C12N 15/82; C12N 15/83
[52] U.S. Cl. .................. 435/172.3; 435/69.1; 435/320.1; 435/418; 435/419; 536/23.72; 536/24.1
[58] Field of Search ................................ 536/24.1, 23.72, 536/69.1; 435/172.3, 320.1, 418, 419

[56] References Cited

U.S. PATENT DOCUMENTS 5,352,605  10/1994  Fraley et al. .......................... 435/240.4
5,530,196   6/1996  Fraley et al. .......................... 800/205

OTHER PUBLICATIONS

Howell et al. 1981. Nature 293:483–486.
Kim et al. 1994. Plant Mol. Biol. 24:105–117.
Barton et al. 1983. Cell 32:1033–1043.
Barker et al. 1983. Plant Mol. Biol. 2:335–350.
Herrera–Estrella et al. 1983. Nature 303:209–213.

*Primary Examiner*—David T. Fox
*Attorney, Agent, or Firm*—Lawrence M. Lavin, Jr.; Arnold, White & Durkee

[57] ABSTRACT

In one aspect the present invention relates to the use of viral promoters in the expression of chimeric genes in plant cells. In another aspect this invention relates to chimeric genes which are capable of being expressed in plant cells, which utilize promoter regions derived from viruses which are capable of infecting plant cells. One such virus comprises the cauliflower mosaic virux (CaMV). Two different promoter regions have been derived from the CaMV genome and ligated to heterologous coding sequences to form chimeric genes. These chimeric genes have been shown to be expressed in plant cells. This invention also relates to plant cells, plant tissue, and differentiated plants which contain and express the chimeric genes of this invention.

6 Claims, 10 Drawing Sheets

CHIMERIC GENES FOR TRANSFORMING PLANT CELLS USING VIRAL PROMOTERS

RELATED APPLICATIONS

This is a continuation of application Ser. No. 08/300,029 filed Sep. 2, 1994, now U.S. Pat. No. 5,530,196, which is a continuation of Ser. No. 08/146,621, filed Oct. 28, 1993, now U.S. Pat. No. 5,352,605, which is a continuation of Ser. No. 07/625,637, filed Dec. 7, 1990, abandoned, which is a continuation of Ser. No. 06/931,492, filed Nov. 17, 1986, abandoned, which is a continuation-in-part of Ser. No. 06/485,568 filed Apr. 15, 1983, abandoned, which is a continuation-in-part of Ser. No. 06/458,414 filed Jan. 17, 1983, abandoned.

TECHNICAL FIELD

This invention is in the fields of genetic engineering and plant biology.

BACKGROUND ART

A virus is a microorganism comprising single or double stranded nucleic acid (DNA or RNA) contained within a protein (and possibly lipid) shell called a "capsid" or "coat". A virus is smaller than a cell, and it does not contain most of the components and substances necessary to conduct most biochemical processes. Instead, a virus infects a cell and uses the cellular processes to reproduce itself.

The following is a simplified description of how a DNA-containing virus infects a cell; RNA viruses will be disregarded in this introduction for the sake of clarity. First, a virus attaches to or enters a cell, normally called a "host" cell. The DNA from the virus (and possibly the entire viral particle) enters the host cell where it usually operates as a plasmid (a loop of extra-chromosomal DNA). The viral DNA is transcribed into messenger RNA, which is translated into one or more polypeptides. Some of these polypeptides are assembled into new capsids, while others act as enzymes to catalyze various biochemical reactions. The viral DNA is also replicated and assembled with the capsid polypeptides to form new viral particles. These viral particles may be released gradually by the host cell, or they may cause the host cell to lyse and release them. The released viral particles subsequently infect new host cells. For more background information on viruses see, e.g., Stryer, 1981 and Matthews, 1970 (note: all references cited herein, other than patents, are listed with citations after the examples).

As used herein, the term "virus" includes phages and viroids, as well as replicative intermediates. As used herein, the phrases "viral nucleic acid" and DNA or RNA derived from a "virus" are construed broadly to include any DNA or RNA that is obtained or derived from the nucleic acid of a virus. For example, a DNA strand created by using a viral RNA strand as a template, or by chemical synthesis to create a known sequence of bases determined by analyzing viral DNA, would be regarded as viral nucleic acid.

The host range of any virus (i.e., the variety of cells that a type of virus is capable of infecting) is limited. Some viruses are capable of efficient infection of only certain types of bacteria; other viruses can infect only plants, and may be limited to certain genera; some viruses can infect only mammalian cells. Viral infection of a cell requires more than mere entry of the viral DNA or RNA into the host cell; viral particles must be reproduced within the cell. Through various assays, those skilled in the art can readily determine whether any particular type of virus is capable of infecting any particular genus, species, or strain of cells. As used herein, the term "plant virus" is used to designate a virus which is capable of infecting one or more types of plant cells, regardless of whether it can infect other types of cells.

With the possible exception of viroids (which are poorly understood at present), every viral particle must contain at least one gene which can be "expressed" in infected host cells. The expression of a gene requires that a segment of DNA or RNA must be transcribed into or function as a strand of messenger RNA (mRNA), and the mRNA must be translated into a polypeptide. Most viruses have about 5 to 10 different genes, all of which are expressed in a suitable host cell.

In order to be expressed in a cell, a gene must have a promoter which is recognized by certain enzymes in the cell. Gene promoters are discussed in some detail in the parent application Ser. No. 458,414 cited above, now abandoned, the contents of which are incorporated herein by reference. Those skilled in the art recognize that the expression of a particular gene to yield a polypeptide is dependent upon two distinct cellular processes. A region of the 5' end of the gene called the promoter, initiates transcription of the gene to produce a mRNA transcript. The mRNA is then translated at the ribosomes of the cell to yield an encoded polypeptide. Therefore, it is evident that although the promoter may function properly, ultimate expression of the polypeptide depends at least in part on post-transcriptional processing of the mRNA transcript.

Promoters from viral genes have been utilized in a variety of genetic engineering applications. For example, chimeric genes have been constructed using various structural sequences (also called coding sequences) taken from bacterial genes, coupled to promoters taken from viruses which can infect mammalian cell(the most commonly used mammalian viruses are designated as Simian Virus 40 (SV40) and Herpes Simplex Virus (HSV)). These chimeric genes have been used to transform mammalian cells. See, e.g., Mulligan et al 1979; Southern and Berg 1982. In addition, chimeric genes using promoters taken from viruses which can infect bacterial cells have been used to transform bacterial cells; see, e.g., the phage lambda $P_L$ promoter discussed in Maniatis et al, 1982.

Several researchers have theorized that it might be possible to utilize plant viruses as vectors for transforming plant cells. See, e.g., Hohn et al, 1982. In general, a "vector" is a DNA molecule useful for transferring one or more genes into a cell. Usually, a desired gene is inserted into a vector, and the vector is then used to infect the host cell.

Several researchers have theorized that it might be possible to create chimeric genes which are capable of being expressed in plant cells, by using promoters derived from plant virus genes. See, e.g., Hohn et al, 1982, at page 216.

However, despite the efforts of numerous research teams, prior to this invention no one had succeeded in(1) creating a chimeric gene comprising a plant virus promoter coupled to a heterologous structural sequence and (2) demonstrating the expression of such a gene in any type of plant cell.

CAULIFLOWER MOSAIC VIRUS (CaMV)

The entire DNA sequence of CaMV has been published. Gardner et al, 1981; Hohn et al, 1982. In its most common form, the CaMV genome is about 8000 bp long. However, various naturally occurring infective mutants which have deleted about 500 bp have been discovered; see Howarth et al 1981. The entire CaMV genome is transcribed into a single mRNA, termed the "full-length transcript" having a sedimentation coefficient of about 35S. The promoter for the full-length mRNA (hereinafter referred to as "CaMV(35S)") is located in the large intergenic region about 1 kb counter-clockwise from Gap 1 (see Guilley et al, 1982).

CaMV is believed to generate at least eight proteins; the corresponding genes are designated as Genes I through VIII. Gene VI is transcribed into mRNA with a sedimentation coefficient of 19S. The 19S mRNA is translated into a protein designated as P66, which is an inclusion body protein. The 19S mRNA is promoted by the 19S promoter, located about 2.5 kb counter-clockwise from Gap 1.

SUMMARY OF THE INVENTION

In one aspect, the present invention relates to the use of viral promoters in the expression of chimeric genes in plant cells. In another aspect this invention relates to chimeric genes which are capable of being expressed in plant cells, which utilize promoter regions derived from viruses which are capable of infecting plant cells. One such virus comprises the cauliflower mosaic virus (CaMV). Two different promoter regions have been derived from the CaMV genome and ligated to heterologous coding sequences to form chimeric genes. These chimeric genes have been proven to be expressed in plant cells. This invention also relates to plant cells, plant tissue (including seeds and propagules), and differentiated plants which have been transformed to contain viral promoters and express the chimeric genes of this invention, and to polypeptides that are generated in plant cells by the chimeric genes of this invention.

BRIEF DESCRIPTION OF THE DRAWINGS

The figures herein are schematic representations; they have not been drawn to scale.

DETAILED DESCRIPTION OF THE INVENTION

Figure 1:
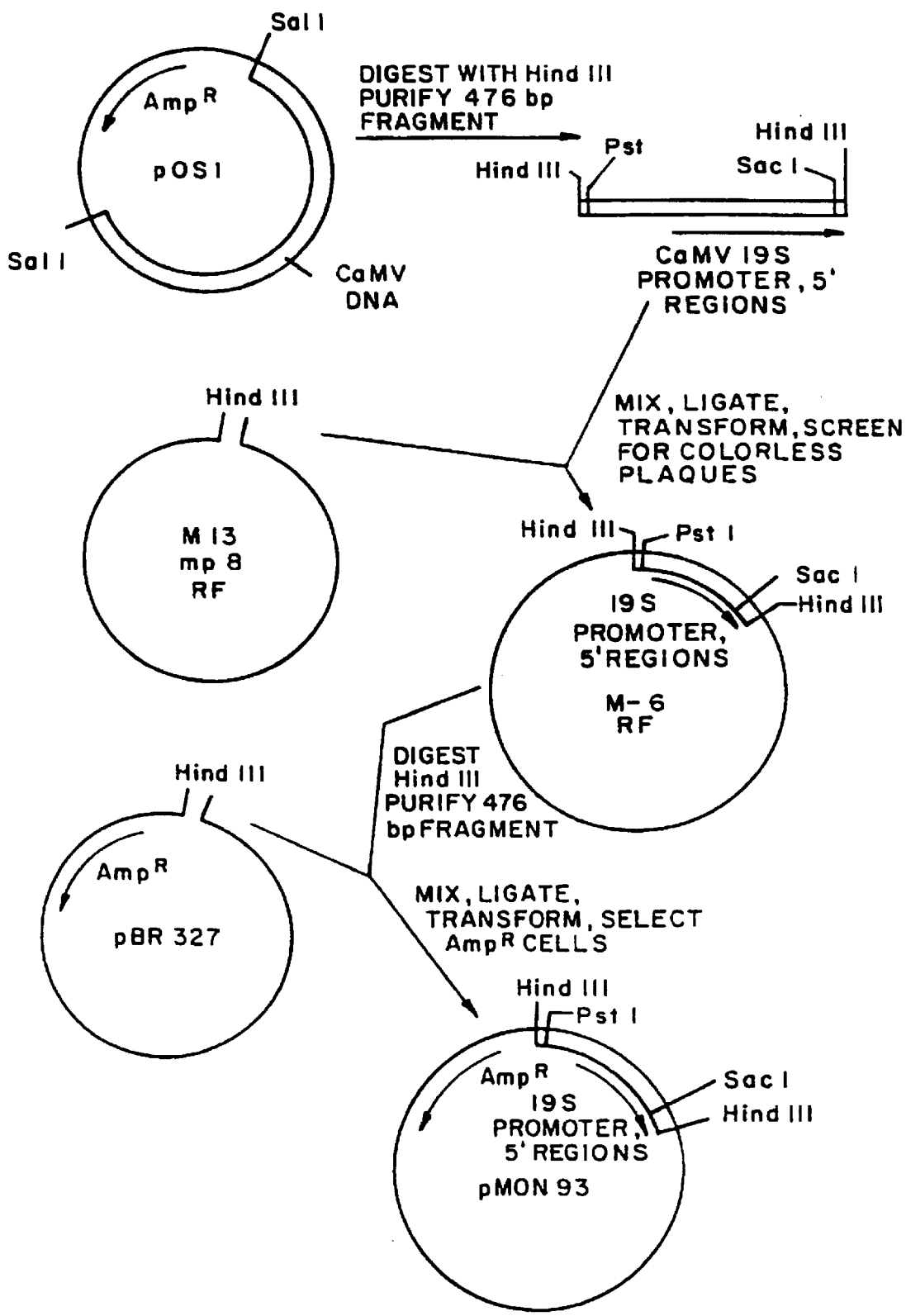
FIG. 1 represents the creation and structure of plasmid pMON93.

In one preferred embodiment of this invention, a chimeric gene was created which contained the following elements:

1. a promoter region and a 5' non-translated region derived from the CaMV (19S) gene, which codes for the P66 protein;
2. a partial coding sequence from the CaMV (19S) gene, including an ATG start codon and several internal ATG sequences, all of which were in the same frame as a TGA termination sequence immediately inside the desired ATG start codon of the NPTII gene;
3. a structural sequence derived from a neomycin phosphotransferase II (NPTII) gene; this sequence was preceded by a spurious ATG sequence, which was in the same reading frame as a TGA sequence within the NPTII structural sequence; and,
4. a 3' non-translated region, including a poly-adenylation signal, derived from a nopaline synthase (NOS) gene.

This chimeric gene, referred to herein as the CaMV(19S)-NPTII-NOS gene, was inserted into plasmid pMON120 (described in the parent application, Ser. No. 458,414; ATCC accession number 39263) to create a plasmid designated as pMON156. Plasmid pMON156 was inserted into an *Agrobacterium tumefaciens* cell, where it formed a co-integrate Ti plasmid by means of a single crossover event with a Ti plasmid in the *A. tumefaciens* cell, using a method described in the parent application. The chimeric gene in the co-integrate plasmid was within a modified T-DNA region in the Ti plasmid, surrounded by left and right T-DNA borders.

*A. tumefaciens* cells containing the co-integrate Ti plasmids with the CaMV(19S)-NPTII-NOS genes were used to infect plant cells, using a method described in the parent application. Some of the plant cells were genetically transformed, causing them to become resistant to an antibiotic (kanamycin) at concentrations which are toxic to untransformed plant cells.

A similar chimeric gene was created and assembled in a plasmid designated as pMON155. This chimeric gene resembled the gene in pMON156, with two exceptions:

1. an oligonucleotide linker having stop codons in all three reading frames was inserted between the CaMV (19S) partial structural sequence and the NPTII structural sequence; and,
2. the spurious ATG sequence on the 5' side of the NPTII structural sequence was deleted.

The construction of this chimeric gene is described in Example 2. This gene was inserted into *A. tumefaciens* cells and subsequently into plant cells. Its level of expression was apparently higher than the expression of the similar gene in pMON156, as assayed by growth on higher concentrations of kanamycin.

CREATION OF PLASMIDS pMON183 and 184; CaMV(35S)

In an alternate preferred embodiment of this envention, a chimeric gene was created comprising (1) a promoter region which causes transcription of the 35S mRNA of cauliflower mosaic virus, CaMV(35S);

(2) a structural sequence which codes for NPTII; and (3) a nopaline synthase (NOS) 3' non-translated region.

The assembly of this chimeric gene is described in Example 3. This gene was inserted into plant cells and it caused them to become resistant to kanamycin.

Petunia plants cannot normally be infected by CaMV. Those skilled in the art may determine through routine experimentation whether any particular plant viral promoter (such as the CAMV promoter) will function at satisfactory levels in any particular type of plant cell, including plant cells that are outside of the normal host range of the virus from which the promoter was derived.

It is possible to regenerate genetically transformed plant cells into differentiated plants. One method for such regeneration was described in U.S. patent application entitled "Genetically Transformed Plants", Ser. No. 458,402, now abandoned. That application was filed simultaneously with, and incorporated by reference into, the parent application of this invention. The methods of application Ser. No. 458,402, now abandoned, may be used to create differentiated plants (and their progeny) which contain and express chimeric genes having plant virus promoters.

It is possible to extract polypeptides generated in plant cells by chimeric genes of this invention from the plant cells, and to purify such extracted polypeptides to a useful degree of purity, using methods and substances known to those skilled in the art.

Those skilled in the art will recognize, or may ascertain using no more than routine experimentation, numerous equivalents to the specific embodiments described herein. Such equivalents are within the scope of this invention, and are covered by the claims below.

EXAMPLES

Example 1

Creation and Use of pMON156

Plasmids which contained CaMV DNA were a gift to Monsanto Company from Dr. R. J. Shepherd, University of California, Davis. To the best of Applicants' knowledge and belief, these plasmids (designated as pOS1) were obtained by inserting the entire genome of a CaMV strain designated as CM4-184 (Howarth et al, 1981) into the Sal I restriction site of a pBR322 plasmid (Bolivar et al, 1978). *E. coli* cells transformed with pOS1 were resistant to ampicillin ($Amp^R$) and sensitive to tetracycline ($Tet^S$).

Figure 2:
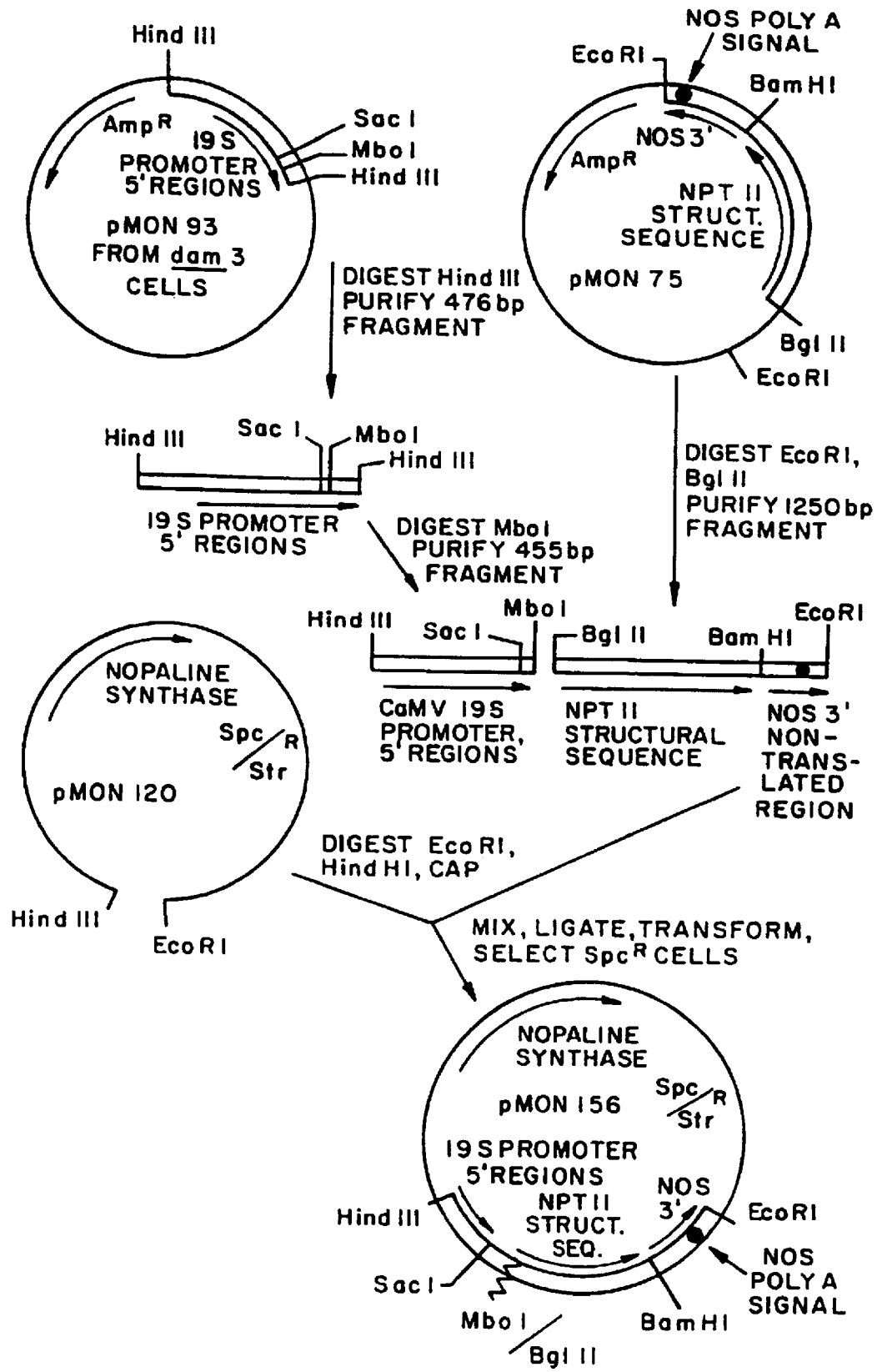
FIG. 2 represents the creation and structure of plasmid pMON156.
Figure 9:
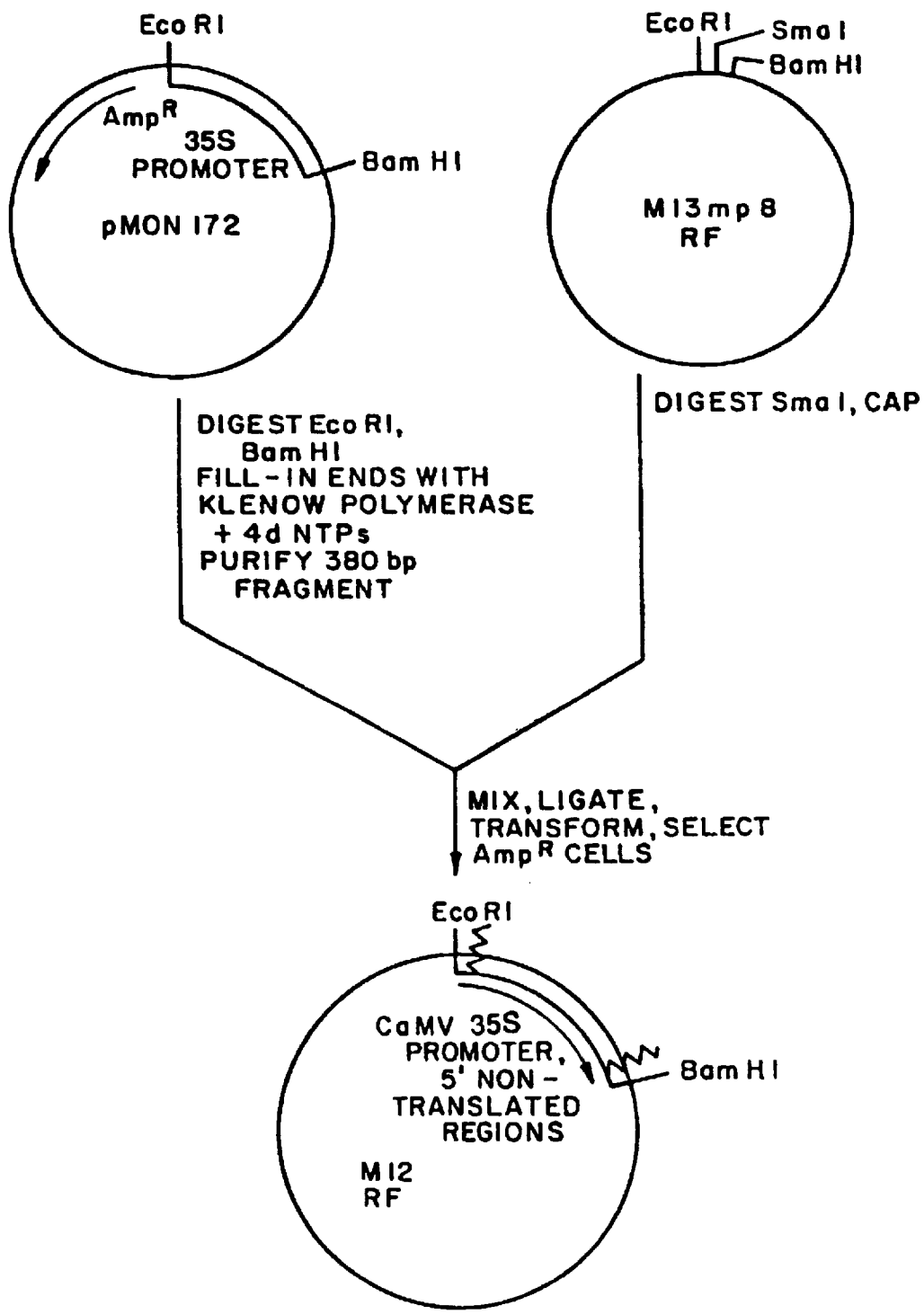
FIG. 9 represents the creation and structure of phage M12.
Figure 10:
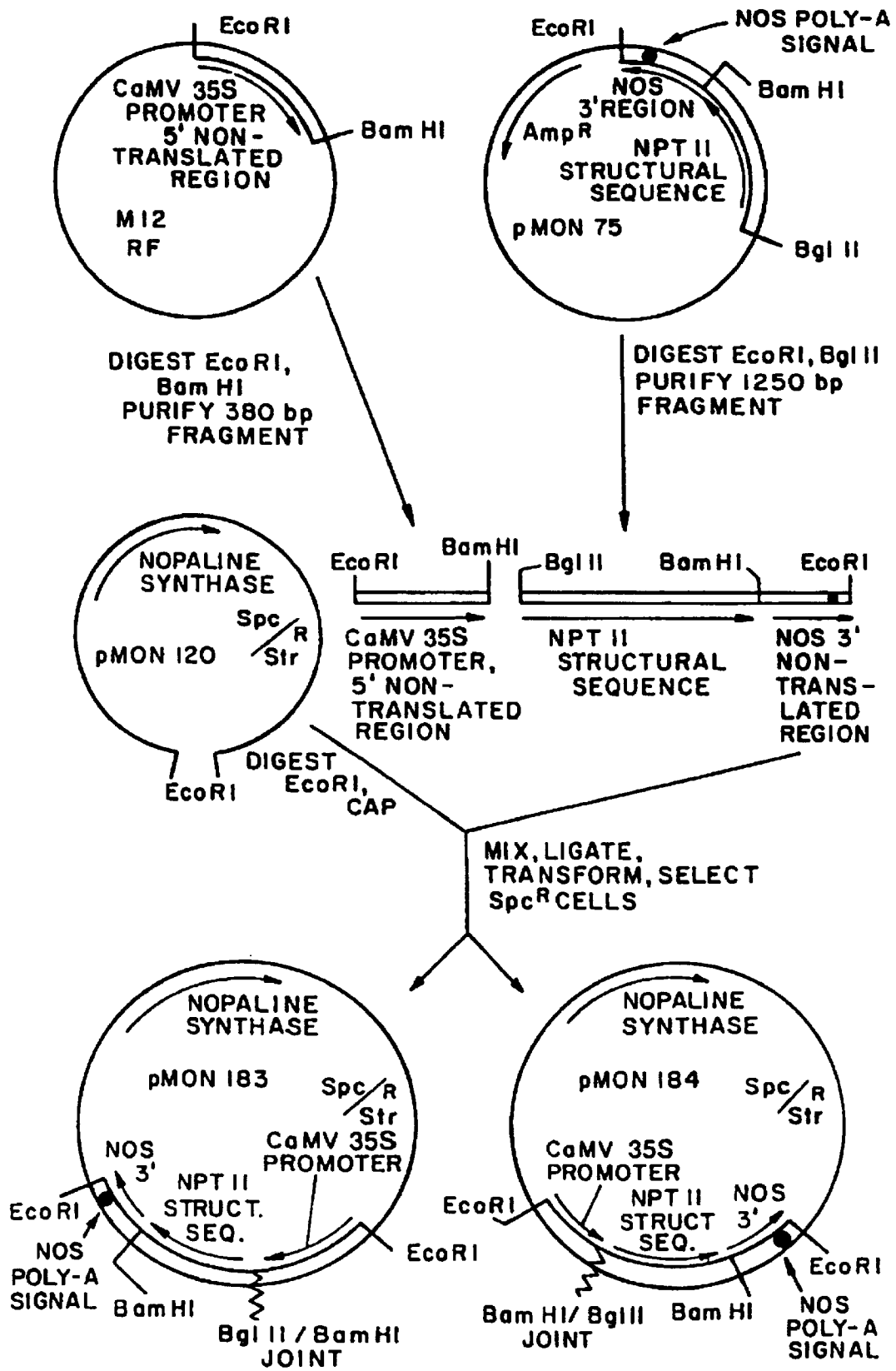
FIG. 10 represents the creation and structure of plasmids pMON183 and pMON184.

Various strains of CaMV suitable for isolation of CaMV DNA which can be used in this invention are publicly available; see, e.g., ATCC Catalogue of Strains II, p. 387 (3rd edition, 1981).

pOS1 DNA was cleaved with HindIII. Three small fragments were purified after electrophoresis on an 0.8% agarose gel using NA-45 membrane (Schleicher and Schuell, Keene N. H.). The smallest fragment, about 500 bp in size, contains the 19S promoter. This fragment was further purified on a 6% acrylamide gel. After various manipulations which did not change the sequence of this fragment (shown in FIG. 1), it was digested with MboI to created 455 bp HindIII-MboI fragment. This fragment was mixed with a 1250 bp fragment obtained by digesting pMON75 (described and shown in FIG. 9 of the parent application Ser. No. 458,414, now abandoned) with BglII and EcoRI. This fragment contains the NPTII structural sequence and the NOS 3' non-translated region. The two fragments were ligated by their compatible MboI and BglII overhangs to create a fragment containing the CaMV(19S)-NPTII-NOS chimeric gene. This fragment was inserted into pMON120 (described and shown in FIG. 10 of the parent application, Ser. No. 458,414, now abandoned; ATCC accession number 39263) which had been cleaved with HindIII and EcoRI. The resulting plasmid was designated as pMON156, as shown in FIG. 2.

Plasmid pMON156 was inserted into *E. coli* cells and subsequently into *A. tumefaciens* cells where it formed a co-integrate Ti plasmid having the CaMV(19S)-NPTII-NOS chimeric gene surrounded by T-DNA borders. *A. tumefaciens* cells containing the co-integrate plasmids were co-cultivated with petunia cells. The foregoing methods are described in detail in a separate application, entitled "Plasmids for Transforming Plant Cells" Ser. No. 458,411, which was filed simultaneously with and incorporated by reference into parent application, Ser. No. 458,414, now abandoned.

The co-cultivated petunia cells were cultured on media containing kanamycin, an antibiotic which is toxic to petunia cells. Kanamycin is inactivated by the enzyme NPTII, which does not normally exist in plant cells. Some of the co-cultivated petunia cells survived and produced colonies on media containing up to 50 ug/ml kanamycin. This indicated that the CaMV(19S)-NPTII-NOS genes were expressed in petunia cells. These results were confirmed by Southern blot analysis of transformed plant cell DNA.

Example 2

Creation of pMON155

Plasmid pMON72 was obtained by inserting a 1.8 kb HindIII-BamHI fragment from bacterial transposon Tn5 (which contains an NPTII structural sequence) into a $PstI^-$ pBR327 plasmid digested with HindIII and BamHI. This plasmid was digested with BglII and PstI to remove the NPTII structural sequence.

Plasmid pMON1001 (described and shown in FIG. 6 of the parent application) from $dam^-$ cells was digested with BglII and PstI to obtain a 218 bp fragment with a partial NPTII structural sequence. This fragment was digested with MboI to obtain a 194 bp fragment.

Figure 3:
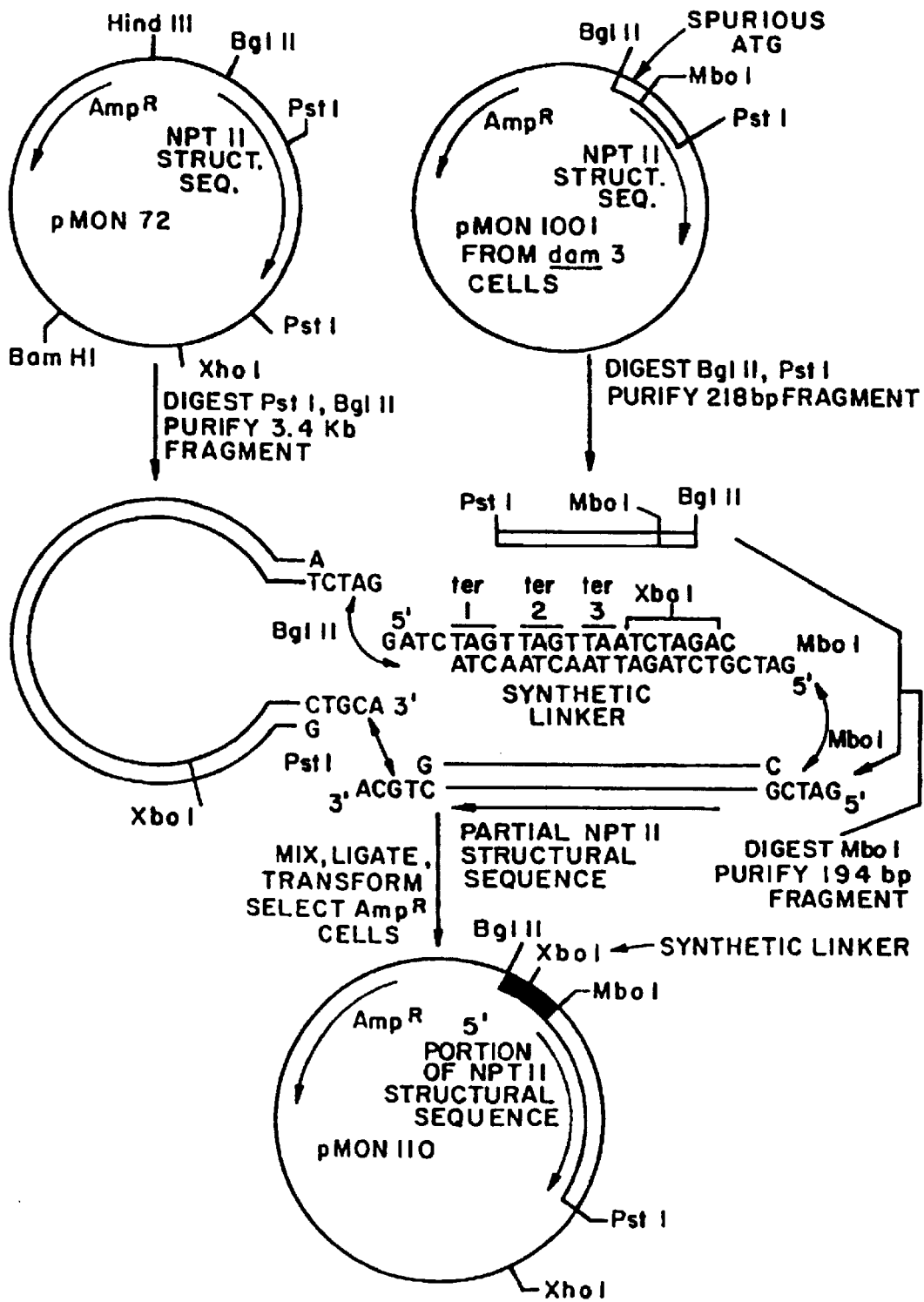
FIG. 3 represents the creation and structure of plasmid pMON110.

A triple ligation was performed using (a) the large PstI-BglII fragment of pMON72; (b) PstI-MboI fragment from pMON1001; and (c) a synthetic linker with BglII and MboI ends having stop codons in all three reading frames. After transformation of *E. coli* cells and selection for ampicillin resistant colonies, plasmid DNA from $Amp^R$ colonies was analyzed. A colony containing a plasmid with the desired structure was identified. This plasmid was designated pMON110, as shown on FIG. 3.

Figure 4:
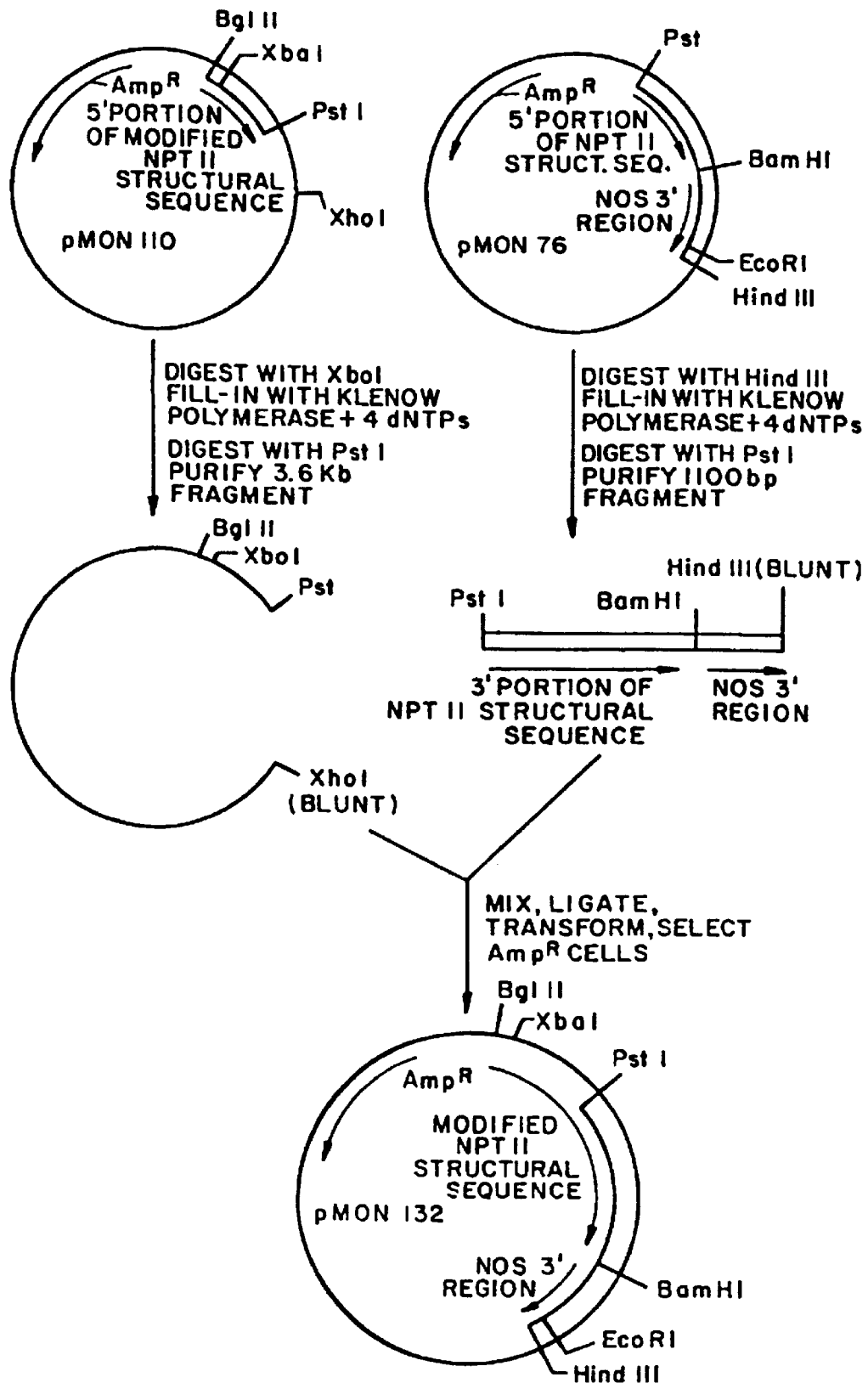
FIG. 4 represents the creation and structure of plasmid pMON132.

In order to add the 3' end of the NPTII structural sequence to the 5' portion in pMON110, pMON110 was treated with XhoI. The resulting overhanging end was filled in to create a blunt end by treatment with Klenow polymerase and the four deoxy-nucleotide triphosphates (dNTP's), A, T, C, and G. The Klenow polymerase was inactivated by heat, the fragment was digested with PstI, and a 3.6 kb fragment was purified. Plasmid pMON76 (described and shown in FIG. 9 of the parent application) was digested with HindIII, filled in to create a blunt end with Klenow polymerase and the four dNTP's, and digested with PstI. An 1100 bp fragment was purified, which contained part of the NPTII structural sequence, and a nopaline synthase (NOS) 3' non-translated region. This fragment was ligated with the 3.6 kb fragment from pMON110. The mixture was used to transform *E. coli* cells; Amp R cells were selected, and a colony having a plasmid with the desired structure was identified. This plasmid was designated pMON132, as shown on FIG. 4. Plasmid pMON93 (shown on FIG. 1) was digested with HindIII, and a 476 bp fragment was isolated. This fragment was digested with MboI, and a 455 bp HindIII-MboI fragment was purified which contained the CaMV (19S) promoter region, and 5' non-translated region. Plasmid pMON132 was digested with EcoRI and BglII to obtain a 1250 bp fragment with (1) the synthetic linker equipped with stop codons in all three reading frames; (2) the NPTII structural sequence; and (3) the NOS 3' non-translated region. These two fragments were joined together through the compatible MboI nd BglII ends to create a CaMV (19S)-NPTII-NOS chimeric gene.

Figure 5:
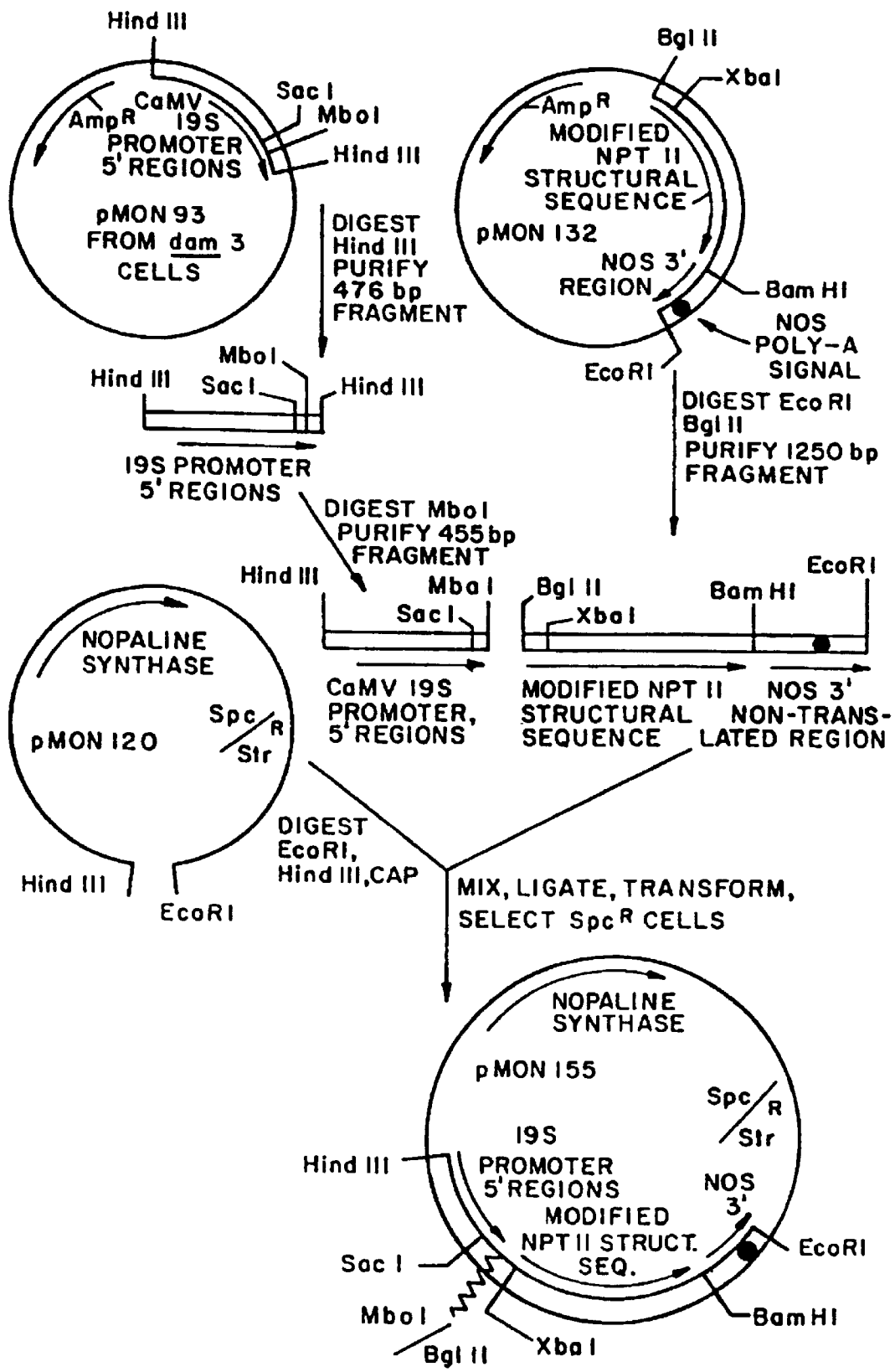
FIG. 5 represents the creation and structure of plasmid pMON155.

This gene was inserted into pMON120, which was digested with HindIII and EcoRI, to create plasmid pMON155, as shown in FIG. 5.

Plasmid pMON155 was inserted into *A. tumefaciens* GV3111 cells containing a Ti plasmid, pTiB6S3. The pMON155 plasmid formed a cointegrate plasmid with the Ti plasmid by means of a single crossover event. Cells which contain this co-integrate plasmid have been deposited with the American Type Culture Center, and have been assigned ATCC accession number 39336. A fragment which contains the chimeric gene of this invention can be obtained by digesting the co-integrate plasmid with HindIII and EcoRI, and purifying the 1.7 kb fragment. These cells have been used to transform petunia cells, allowing the petunia cells to grow on media containing at least 100 ug/ml kanamycin.

Example 3

Creation of pMON183 and 184

Plasmid pOS1 (described in Example 1) was digested with BglII, and a 1200 bp fragment was purified. This fragment contained the 35S promoter region and part of the 5' non-translated region. It was inserted into plasmid pSHL72 which had been digested with BamHI and BglII (pSHL72 is functionally equivalent to pAGO60, described in Colbere-Garapin et al, 1981). The resulting plasmid was designated as pMON50, as shown on FIG. 6.

Figure 6:
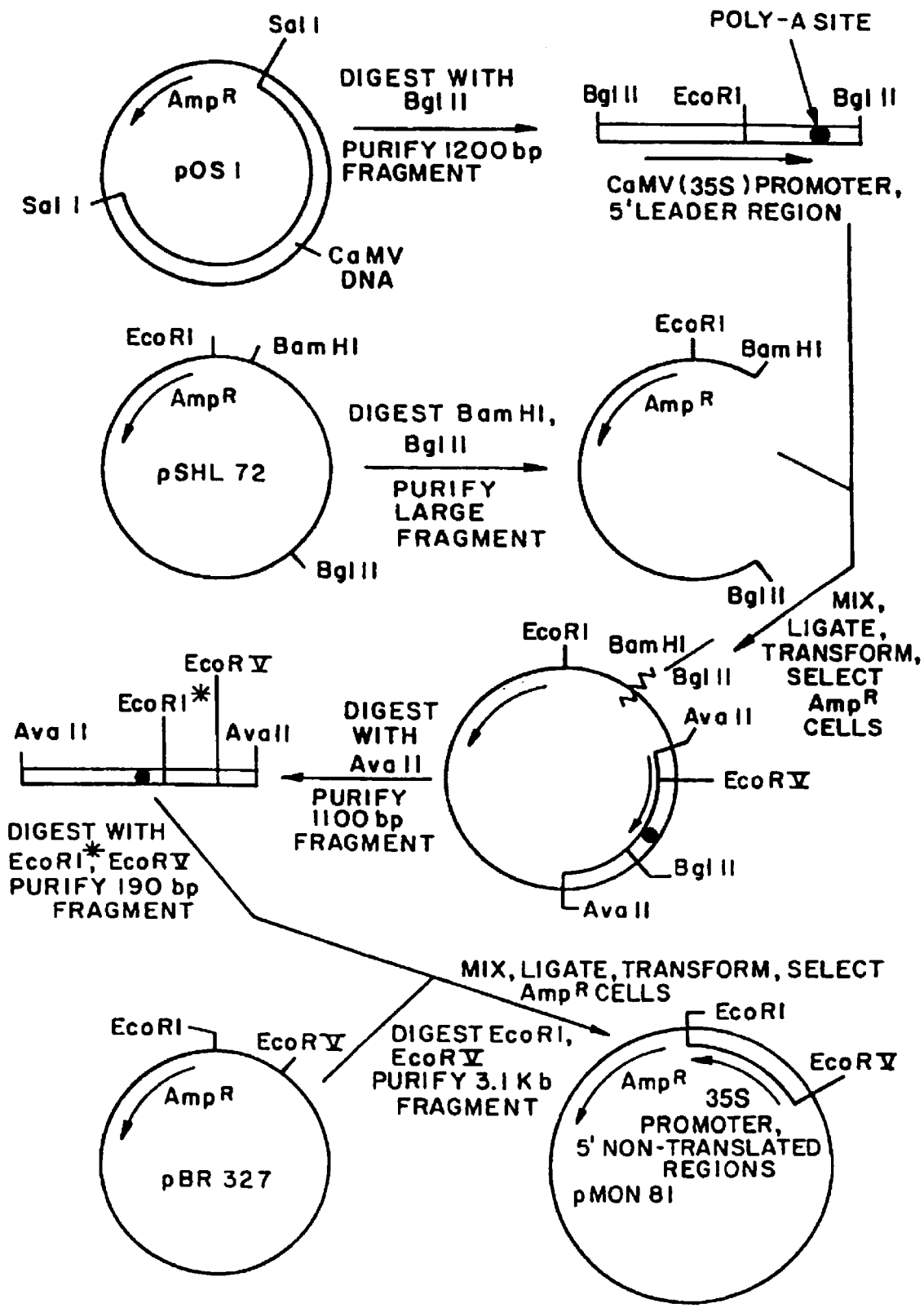
FIG. 6 represents the creation and structure of plasmid pMON81.

The cloned BglII fragment contains a region of DNA that acts as a polyadenylation site for the 35S RNA transcript. This polyadenylation region was removed as follows: pMON50 was digested with AvaII and an 1100 bp fragment was purified. This fragment was digested with EcoRI* and EcoRV. The resulting 190 bp EcoRV-EcoRI* fragment was purified and inserted into plasmid pBR327, which had been digested with EcoRI* and EcoRV. The resulting plasmid, pMON81, contains the CaMV 35S promoter on a 190 bp EcoRV-EcoRI* fragment, as shown in FIG. 6.

Figure 7:
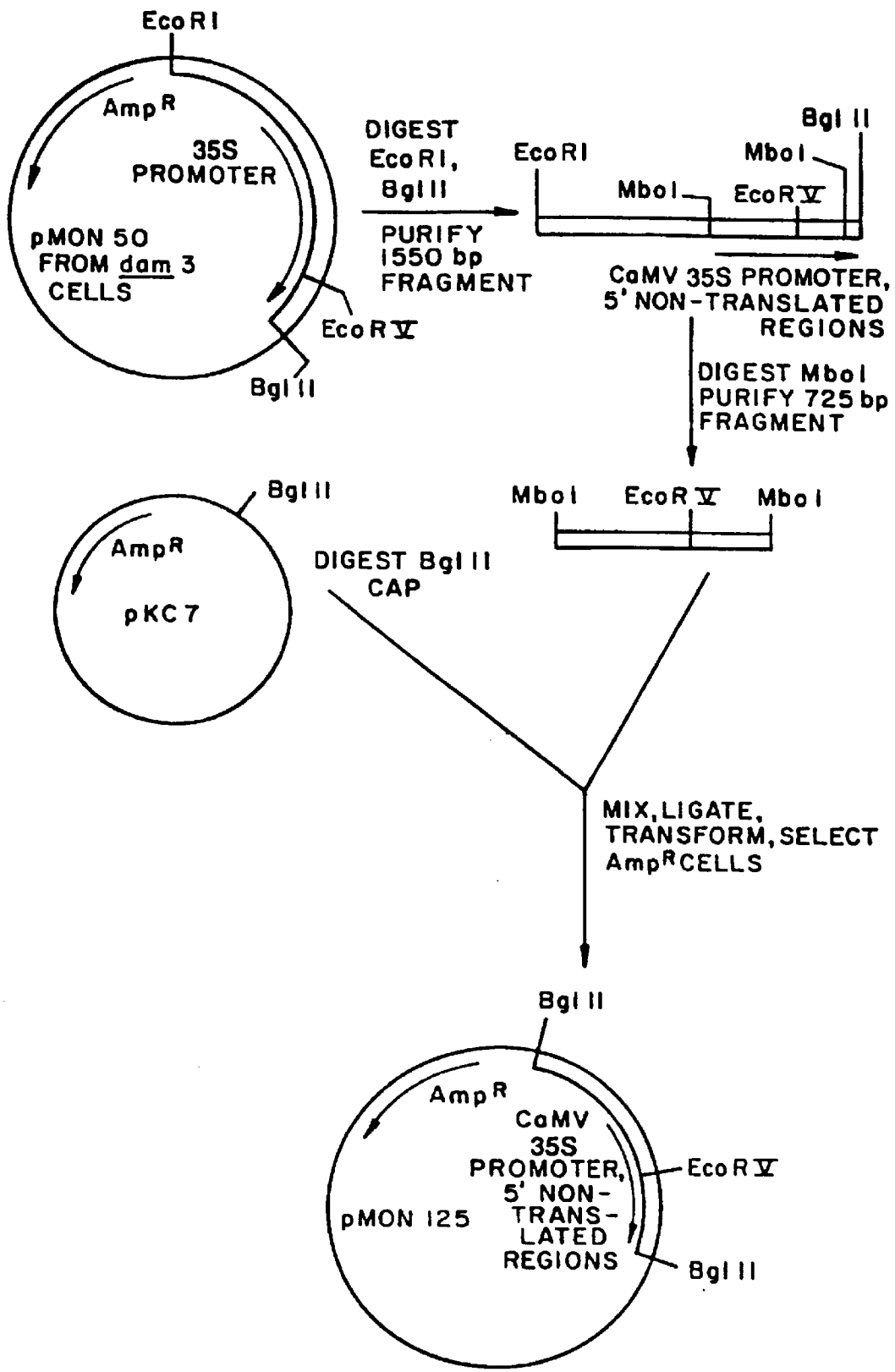
FIG. 7 represents the creation and structure of plasmid pMON125.

To make certain the entire promoter region of CaMV (35S) was present in pMON81, a region adjacent to the 5' (EcoRV) end of the fragment was inserted into pMON81 in the following way. Plasmid pMON50 prepared from dam⁻ cells was digested with EcoRI and BglII and the resultant 1550 bp fragment was purified and digested with MboI. The resulting 725 bp MboI fragment was purified and inserted into the unique BglII site of plasmid pKC7 (Rao and Rogers, 1979) to give plasmid pMON125, as shown in FIG. 7. The sequence of bases adjacent to the two MboI ends regenerates BglII sites and allows the 725 bp fragment to be excised with BglII.

Figure 8:
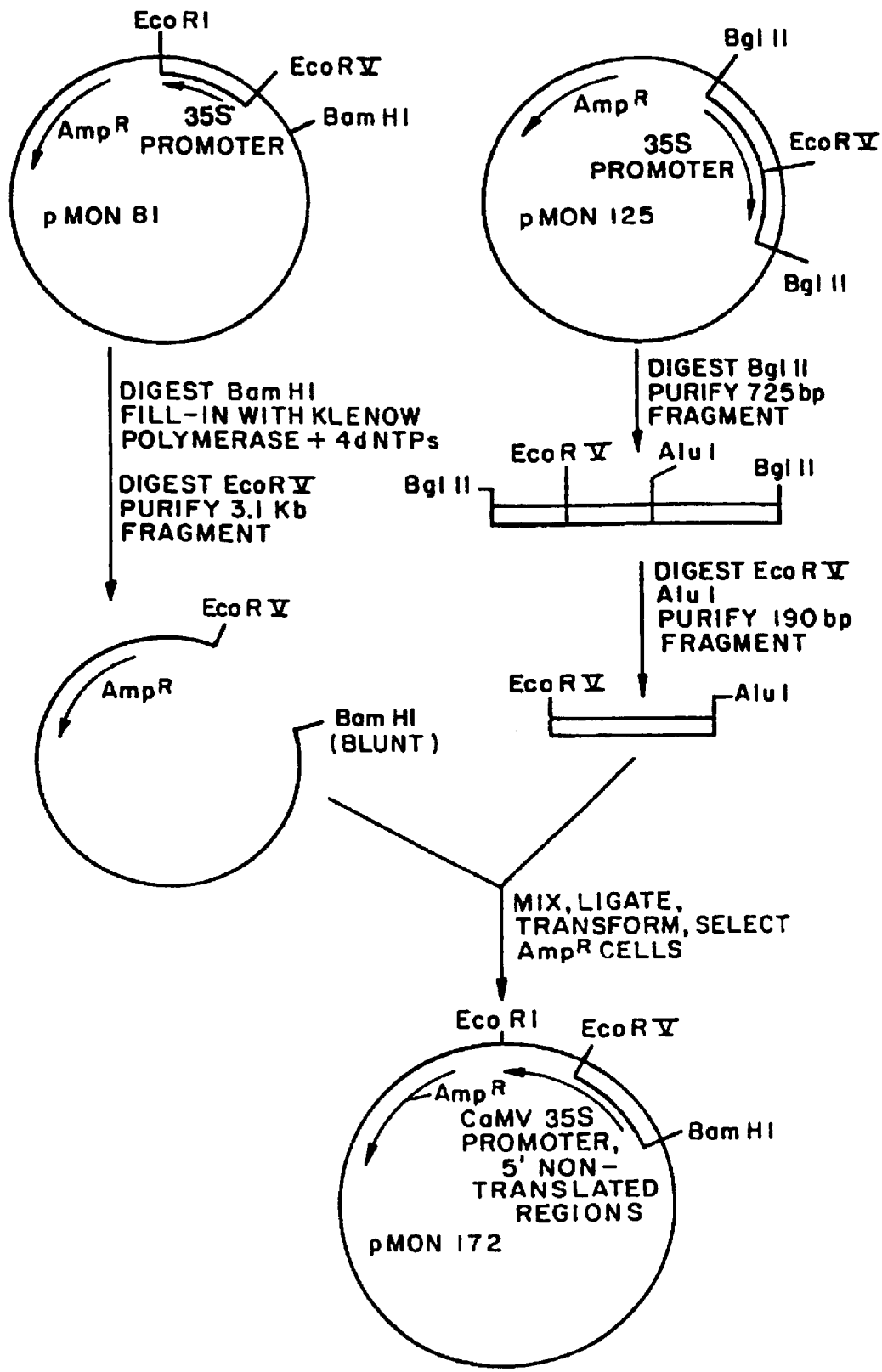
FIG. 8 represents the creation and structure of plasmid pMON172.

To generate a fragment carrying the 35S promoter, the 725 bp BglII fragment was purified from pMON125 and was subsequently digested with EcoRV and AluI to yield a 190 bp fragment. Plasmid pMON81 was digested with BamHI, treated with Klenow polymerase and digested with EcoRV. The 3.1 kb EcoRV-BamHI(blunt) fragment was purified, mixed with the 190 bp EcoRV-AluI fragment and treated with DNA ligase. Following transformation and selection of ampicillin-resistant cells, plasmid pMON172 was obtained which carries the CaMV(35S) promoter sequence on a 380 bp BamHI-EcoRI fragment, as shown on FIG. 8. This fragment does not carry the polyadenylation region for the 35S RNA. Ligation of the AluI end to the filled-in BamHI site regenerates the BamHI site.

To rearrange the restriction endonuclease sites adjacent to the CaMV(35S) promoter, the 380 bp BamHI-EcoRI fragment was purified from pMON172, treated with Klenow polymerase, and inserted into the unique SmaI site of phage M13 mp8. One recombinant phage, M12, carried the 380 bp fragment in the orientation shown on FIG. 9. The replicative form DNA from this phage carries the 35S promoter fragment on an EcoRI(5')-BamHI(3') fragment, illustrated below.

Plasmids carrying a chimeric gene CaMV(35S) promoter region-NPTII structural sequence-NOS 3' non-translated region) were assembled as follows. The 380 bp EcoRI-BamHI CaMV(35S) promoter fragment was purified from phage M12 RF DNA and mixed with the 1250 bp BglII-EcoRI NPTII-NOS fragment from pMON75. Joining of these two fragments through their compatible BamHI and BglII ends results in a 1.6 kb CaMV(35S)-NPTII-NOS chimeric gene. This gene was inserted into pMON120 at the EcoRI site in both orientations. The resultant plasmids, pMON183 and 184, appear in FIG. 10. These plasmids differ only in the direction of the chimeric gene orientation.

These plasmids were used to transform petunia cells, as described in Example 1. The transformed cells are capable of growth on media containing 100 ug/ml kanamycin.

COMPARISON OF CaMV(35S) AND NOS PROMOTERS

Chimeric genes carrying the nopaline synthase (NOS) promoter or the cauliflower mosaic virus full-length transcript promoter (CaMV(35S)) were constructed. In both cases, the promoters, which contain their respective 5' non-translated regions were joined to a NPTII coding sequence in which the bacterial 5' leader had been modified so that a spurious ATG translational initiation signal (Southern and Berg, 1982) has been removed.

Plasmid pMON200 is a derivative of previously described intermediate vector pMON120 (ATCC accession number 39263). pMON200 contains a modified chimeric nopaline synthase-neomycin phosphotransferase-nopaline synthase gene (NOS/NPTII/NOS) which confers kanamycin ($Km^R$) resistance to the transformed plant. The modified chimeric $Km^R$ gene lacks an upstream ATG codon present in the bacterial leader sequence and a synthetic multilinker with unique HindIII, XhoI, BglII, XbaI, ClaI and EcoRI restriction sites.

Plasmid pMON273 is a derivative of pMON200 in which the nopaline synthase promoter of the chimeric NOS-NPTII-NOS gene has been replaced with the CaMV(35S) promoter.

The CaMV(35S) promoter fragment was isolated from plasmid pOS-1, a derivative of pBR322 carrying the entire genome of CM4-184 as a SalI insert (Howarth et al., 1981). The CM4-184 strain is a naturally occurring deletion mutant of strain CM1841. The nucleotide sequence of the CM1841 (Gardner et al., 1981) and Cabb-S (Franck et al., 1980) strains of CaMV have been published as well as some partial sequence for a different CM4-184 clone (Dudley et al., 1982). The nucleotide sequences of the 35S promoter regions of these three isolates are essentially identical. In the following the nucleotide numbers reflects the sequence of Gardner et al. (1981). The 35S promoter was isolated as an AluI (n 7143)-EcoRI* (n 7517) fragment which was inserted first into pBR322 cleaved with BamHI, treated with the Klenow fragment of DNA polymerase I and then cleaved with EcoRI. The promoter fragment was then excised from pBR322 with BamHI and EcoRI, treated with Klenow polymerase and inserted into the SmaI site of M13 mp8 so that the EcoRI site of the mp8 multilinker was at the 5' end of the promoter fragment. Site directed mutagenesis (Zoller and Smith, 1982) was then used to introduce a G at nucleotide 7464 to create a BglII site. The 35S promoter fragment was then excised from the M13 as a 330 bp EcoRI-BglII site. The 35S promoter fragment was then excised from the M13 as a 330 bp EcoRI-BglII fragment which contains the 35S promoter, 30 nucleotides of the 5' non-translated leader but does not contain any of the CaMV translational initiators nor the 35S transcript polyadenylation signal that is located 180 nucleotides downstream from the start of transcription (Covey et al., 1981; Guilley et al., 1982). The CaMV(35S) promoter sequence described above is listed below.

fuged at 150,000×g for 48 hours. The ethidium bromide was extracted with isopropanol, the DNA was dialyzed, and ethanol precipitated.

Southern Hybridization Analysis 10 ug of each plant DNA was digested, with BamHI for pMON200 plant DNAs and EcoRI for pMON273 plant DNAs. The fragments were separated by electrophoresis on a 0.8% agarose gel and transferred to nitrocellulose (Southern, 1975). The blots were hybridized (50% formamide, 3×SSC, 5× denhardt's, 0.1% SDS and 20 ug/ml tRNA) with nick-translated pMON273 plasmid DNA for 48–60 hours at 42° C.

Preparation of RNA from Plant Tissue

Plant leaves were frozen in liquid nitrogen and ground to a fine powder with a mortar and pestle. The frozen tissue was added to a 1:1 mixture of grinding buffer and PCE (1% Tri-iso-propylnaphtalene-sulfonic acid, 6% p-Aminosalicylic acid, 100 mM NaCl, 1% SDS and 50 mM 2-mercaptoethanol; PCI [phenol: chloroform: isoamyl alcohol (24:24:1)] and homogenized immediately with a polytron. The crude homogenate was mixed for 10 min and the phases separated by centrifugation. The aqueous phase then was re-extracted with an equal volume of PCI. The aqueous phase was ethanol precipitated with one tenth volume of 3M NaAcetate and 2.5 volumes of ethanol. The nucleic acid pellet was resuspended in water. An equal volume of 4M lithium chloride LiCl was added and the mix was placed on ice for 1 hour or overnight. Following centrifugation, the pellet was resuspended in water the LiCl precipitation repeated 3 times. The final LiCl pellet was resuspended in water and ethanol precipitated.

pMON273 CaMV 35S Promoter and 5' Leader

```
    EcoRI
1   |         .            .            .            .            .            .           70
GAATTCCCGATCcTATCTGTCACTTCATCAAAAGGACAGTAGAAAAGGAAGGTGGCACTACAAATGCCAT
71            .            .            .            .            .            .          140
CATTGCGATAAAGGAAAGGCTATCGTTCAAGATGCCTCTGCCGACAGTGGTCCCAAAGATGGACCCCCAC
141           .            .            .            .            .            .          210
CCACGAGGAGCATCGTGGAAAAAGAAGACGTTCCAACCACGTCTTCAAAGCAAGTGGATTGATGTGATAT
                                                                    TATA
211           .            .            .            .            .            |          280
CTCCACTGACGTAAGGGATGACGCACAATCCCACTATCCTTCGCAAGACCCTTCCTCTATATAAGGAAGT
                       5' mRNA                                 BglII
281           .            |            .            .           | 334
TCATTTCATTTGGAGAGGACACGCTGAAATCACCAGTCTCTCTACAAGATCT
```

The 35S promoter fragment was joined to a 1.3 kb BglII-EcoRI fragment containing the Tn5 neomycin phosphotransferase II coding sequence modified so that the translational initiator signal in the bacterial leader sequence had been removed and the NOS 3' non-translated region and inserted into pMON120 to give pMON273.

These plasmids were transferred in *E. coli* strain JM101 and then mated into *Agrobacterium tumefaciens* strain GV3111 carrying the disarmed pTiB6S3-SE plasmid as described by Fraley et al. (1983).

Plant Transformation

Cocultivation of Petunia protoplasts with *A. tumefaciens*, selection of kanamycin resistant transformed callus and regeneration of transgenic plants was carried out as described in Fraley et al. (1984).

Preparation of DNAs

Plant DNA was extracted by grinding the frozen tissue in extraction buffer (50 mM TRIS-HCl pH 8.0, 50 mM EDTA, 50 mM NaCl, 400 ul/ml EtBr, 2% sarcosyl). Following low speed centrifugation, cesium chloride was added to the supernatant (0.85 gm/ml). The CsCl gradients were centri- Poly (A) containing RNA was isolated by passing total RNA over an Oligo d(T) cellulose Type III (Collaborative Research) column. Quantitation of the poly (A) containing RNA involved annealing an aliquot of the RNA to radiolabeled poly U [(uridylate 5,6-3H)-polyuridylic acid] (New England Nuclear), followed by RNase A treatment (10 ug per ml for 30 minutes at 37° C.). The reaction mix was spotted on DE-81 filter paper, washed 4× with 0.5M NaPhosphate (pH 7.5) and counted. Globin poly (A) containing RNA (BRL) was used as a standard.

Northern Hybridization Analysis 5 ug of poly (A) RNA from each plant source was treated with glyoxal and dimethysulfoxide (Maniatis, 1982). The RNAs were electrophoresed in 1.5% agarose gels (0.01M NaH$_2$HPO$_4$, pH 6.5) for 7 hours at 60 volts. The glyoxylated RNAs were electro-blotted (25 mM NaH$_2$PO$_4$/NaHPO$_4$, pH 6.5) for 16 hours at 125 amps from the gel to GeneScreen® (New England Nuclear). The filters were hybridized as per manufacturer's instructions (50% formamide, 0.02% polyvinylpyrrolidone, 0.02% bovine serum albumin, 0.02% ficoll, 5×SSC, 1.0% SDS, 100 u/ml tRNA and probe) for 48–60 hours at 42° C. with constant shaking. The nick-translated DNAs used as probes were the 1.3 kb BglII/EcoRI NPTII fragment purified from the pMON273 plasmid for detecting the NPTII transcript, and the petunia small subunit gene as an internal standard for comparing the amount of RNA per lane. The membranes were washed 2×100 ml of 2×SSC at room temperature for 5 minutes, 2×100 ml of 2×SSC/1.0% SDS at 65° C. for 30 minutes. The membranes were exposed to XAR-5 film with a DuPont intensifying screen at −80° C.

Neomycin Phosphotransferase Assay

The gel overlay assay was used to determine the steady state level of NPTII enzyme activity in each plant. Several parameters were investigated for optimizing the sensitivity of the assay in plant tissue. Early observations showed that the level of NPTII activity varied between leaves from different positions on the same plant. This variability was minimized when the plant extract was made from pooled tissue. A paper hole punch was used to collect 15 disks from both young and old leaves. Grinding the plant tissue in the presence of micro-beads (Ferro Corp) rather than glass beads increased the plant protein yield 4-fold.

To optimize detection of low levels of NPTII activity a saturation curve was prepared with 10–85 ug/lane of plant protein. For the pMON200 (NOS) plants, NPTII activity was not detectable at less than 50 ug/lane of total protein (2 hour exposure) while activity was detectable at 20 ug/lane for the pMON273 plants. There was a non-linear increase in NPTII activity for pMON200 NOS plants between 40 and 50 ug of protein per lane. This suggested that the total amount of protein may affect the stability of the NPTII enzyme. Supplementing plant cell extracts with 30–45 ug per lane of bovine serum albumin (BSA), resulted in a linear response; NPTII activity increased proportionately as plant protein levels increased. The addition of BSA appears to stabilize the enzyme, resulting in a 20-fold increase in the sensitivity of the assay. Experiments indicate that 25 ug/lane of pMON273 plant protein and 70 ug/lane of pMON200 plant protein was within the linear range of the assay in the presence of BSA. Elimination of SDS from the extraction buffer resulted in a 2-fold increase in assay sensitivity. Leaf disks were pooled from each plant for the assay. The tissue was homogenized with a glass rod in a microfuge tube with 150–200 ul of extraction buffer (20% glycerol, 10% β-mercaptoethanol, 125 mM Tris-HCl pH 6.8, 100 ug/ml bromophenol blue and 0.2% SDS). Following centrifugation in a microfuge for 20 minutes, total protein was determined using the Bradford assay. 25 ug of pMON273/3111SE plant protein or 70 ug of pMON200/3111SE plant protein, supplemented with BSA, was loaded on a native polyacrylamide gel as previously described. The polyacrylamide gel was equilibrated for 30 minutes in water and then 30 minutes in reaction buffer (67 mM TRIS-maleate pH 7.1, 43 mM $MgCl_2$, 400 mM $NH_4Cl$), transferred onto a glass plate, and overlaid with a 1.5% agarose gel. The overlay gel contained the neomycin phosphotransferase substrates: 450 uCi [γ-$^{32}$] ATP and 27 ug/ml neomycin sulfate (Sigma). After 1 hour at room temperature a sheet of Whatman P81 paper, two sheets of Whatman 3MM paper, a stack of paper towels and a weight were put on top of the agarose gel. The phosphorylated neomycin is positively charged and binds to the P81 phosphocellulose ion exchange paper. After blotting overnight, the P81 paper was washed 3× in 80° C. water, followed by 7 room temperature washes. The paper was air dried and exposed to XAR-5 film. Activity was quantitated by counting the $^{32}$P-radioactivity in the NPTII spot. The NPTII transcript levels and enzyme activities in two sets of transgenic petunia plants were compared. In one set of plants (pMON273) the NPTII coding sequence is preceded by the CaMV(35S) promoter and leader sequences, in the other set of plants (PMON200) the NPTII coding region is preceded by the nopaline synthase promoter and leader sequences. The data indicates the pMON273 plants contain about a 30 fold greater level of NPTII transcript than the pMON200 plants, see Table I below.

TABLE I

QUANTITATION OF NPTII TRANSCRIPT LEVELS AND NPTII ACTIVITY IN pMON273 AND pMON200 PLANTS

| Plant Number | Relative NPTII Transcript[a] | Relative NPTII Activity[b] |
|---|---|---|
| PMON 273 | | |
| 3272 | 682 | 113 |
| 3271 | 519 | 1148 |
| 3349 | 547 | 447 |
| 3350 | 383 | 650 |
| 3343 | 627 | 1539 |
| Average | 551 | 779 |
| PMON 200 | | |
| 2782 | 0 | 0.22 |
| 2505 | 0 | 5.8 |
| 2822 | 0 | 0 |
| 2813 | 34 | 19 |
| 2818 | 0 | 1.0 |
| 3612 | 45 | 0.33 |
| 2823 | 97 | 23 |
| Average | 19 | 7 |
| | ~30-fold difference | ~110-fold difference |

[a]Numbers derived from silver grain quantitation of autoradiogram. The RNA per lane was determined by filter hybridization to a petunia small subunit gene. The NPTII transcript values obtained with the NPTII probe were normalized for the amount of RNA in each lane.
[b]Numbers represent quantitation of NPT assay. Values were obtained by scintillation counting of 32-P-NPTII spots on the PE-81 paper used in the NPT assay as previously described. Values have been adjusted for the different amounts of protein loaded on the gels (25 ug) for pMON273 and 70 ug for pMON200 plants).

Consistent with this observation is the finding that the pMON273 leaf extracts have higher NPTII enzyme activity than the pMON200 leaf extracts. In several of the transgenic plants, there is a substantial variation in both RNA and enzyme levels which cannot be accounted for by the slight difference in gene copy number. Such "position effects" have been reported in transgenic mice and fruit flies and have not yet been adequately explained at the molecular level. Although, there is not a clear correlation between insert copy number and level of chimeric gene expression, the fact that 4 of the 7 pMON200 transgenic plants contain 2 copies of the NOS-NPTII-NOS gene would suggest that the differential expression of the CaMV(35S) promoter is actually slightly underestimated in these studies.

The constructs described in this comparative example have identical coding regions and 3' non-translated regions, indicating that the differences in the steady state transcript levels of these chimeric genes is a result of the 5' sequences.

COMPARISON OF CAMV19S AND CaMV(35S) PROMOTERS

Chimeric genes were prepared comprising either the CaMV19S or CaMV(35S) promoters. As in the above example, the promoters contained their respective 5' non-translated regions and were joined to a NPTII coding sequence in which the bacterial 5' leader had been modified to remove a spurious ATG translational initiation signal. The constructs tested were pMON203 and pMON204 containing the CaMV19S/NPTII/NOS gene and pMON273 containing the CaMV(35S)/NPTII/NOS gene.

Construction of pMON203

The CaMV 19S promoter fragment was isolated from plasmid pOS-1, a derivative of pBR322 carrying the entire genome of CM4-184 as a SalI insert (Howarth et al., 1981). The CM4-184 strain is a naturally occurring deletion mutant of strain CM1841. The references to nucleotide numbers in the following discussion are those for the sequence of CM1841 (Gardner et al., 1981). A 476 bp fragment extending from the HindIII site at bp 5372 to the HindIII site at bp 5848 was cloned into M13 mp8 for site directed mutagenesis (Zoller and Smith, 1982) to insert an XbaI (5'-TCTAGA) site immediately 5' of the first ATG translational initiation signal in the 19S transcript (Dudley et al., 1982). The resulting 400 bp HindIII-XbaI fragment was isolated and joined to the 1.3 kb XbaI-EcoRI fragment of pMON273 which carries the neomycin phosphotransferase II (NPTII') coding sequence modified so that the extra ATG translational initiation signal in the bacterial leader had been removed and the nopaline synthase 3' nontranslated region (NOS). The resulting 1.7 kb HindIII-EcoRI fragment was inserted into pMON120 between the EcoRI and HindIII sites to give pMON203. The complete sequence of the 19S promoter-NPTII leader is given below.

Quantitation was done by scintillation counting of $^{32}$P-neomycin, the end product of neomycin phosphotransferase activity. The average NPTII enzyme level determined for CaMV(35S) (pMON273) plants was 3.6 times higher than that determined for CaMV(19S) (pMON203 & 204) plants.

QUANTITATION OF NPTII ACTIVITY LEVELS
IN pMON203, pMON204, AND pMON273
PLANTS

| Construct | Plant Number | Relative NPTII Activity[a] | Average |
|---|---|---|---|
| PMON203 | 4283 | 499,064 | 398,134 |
| pMON203 | 4248 | 297,204 | |
| | | | 356,203 |
| pMON204 | 4275 | 367,580 | 314,273 |
| PMON204 | 4280 | 260,966 | |
| pMON273 | 3350 | 1,000,674 | 1,302,731 |
| pMON273 | 3271 | 1,604,788 | |
| $\frac{35s}{19s}$ | $\frac{1,302,721}{356,203} \cong 3.6$ | | |

[a]Numbers represent quantitation of NPT assay. Values were obtained by scintillation counting of $^{32}$P-NPTII spots on the PE-81 paper used in the NPT assay as previously described.

```
    HindIII
1|          .          .          .          .          .          .          70
AAGCTTTAAAGCTGCAGAAAGGAATTACCACAGCAATGACAAAGAGACATTGGCGGTAATAAATACTATA
71          .          .          .          .          .          .          140
AAGAAATTCAGTATTTATCTAACTCCTGTTCATTTTCTGATTAGGACAGATAATACTCATTTCAAGAGTT
141         .          .          .          .          .          .          210
TTGTTAACCTTAATTACAAAGGAGATTCAAAACTTGGAAGAAACATCAGATGGCAAGCATGGCTTAGCCA
211         .          .          .          .          .          .          280
CTATTCGTTTGATGTTGAACATATTAAAGGAACCGACAACCACTTTGCGGACTTCCTTTCAAGAGAATTC
281         .          .          .          .          .          .          350
AATAAGGTTAATTCCTAATTGAAATCCGAAGATAAGATTCCCACACACTTGTGGCTGATATCAAAAAGGC
          TATA                                  5'  mRNA
351         |          .          .          . | | |          402
TACTACCTATATAAACACATCTCTGGAGACTGAGAAAATCAGACCTCCAAGC
    XbaI                NPTII Initiator Signal
    |                   |
TCTAGACGATCGTTTCGC ATG
```

Construction of pMON204

The 400 bp HindIII-XbaI fragment containing the CaMV19S promoter was joined to a synthetic linker with the sequence:

```
        XbaI              BglII
        |                 |
        5'-TCTAGACTCCTTACAACAGATCT
``` to add a BglII site to the 3' end of the promoter fragment. The HindIII-BglII fragment was joined to the 1.3 kb BglII-EcoRI fragment of pMON128 that contains the natural, unmodified NPTII coding sequence joined to the NOS 3' nontranslated signals and inserted into the EcoRI and HindIII sites of pMON120. The resulting plasmid is pMON204. The CaMV 19S promoter signals in this plasmid are identical to those in pMON203. The only difference is the sequence of the 5' nontranslated leader sequence which in pMON204 contains the extra ATG signal found in the bacterial leader of NPTII and contains extra bases from the synthetic linker and bacterial leader sequence.

Petunia leaf discs were transformed and plants regenerated as described above. The gel overlay assay was used to determine NPTII levels in transformants.

REFERENCES

F. Bolivar, *Gene* 4: 121 (1978)
F. Colbere-Garapin et al, *J. Mol. Biol.* 150: 1 (1981)
S. N. Covey, G. P. Lomonosoff and R. Hull (1981) *Nucleic Acids Res.* 9, 6735–6747.
R. Dudley et al (1982) *Virology* 117:19.
R. T. Fraley, et al. (1983) *Proc. Natl. Acad. Sci.* USA 80:4803–4807.
R. T. Fraley, R. B. Horsch, A. Matzke, M. D. Chilton, W. S. Chilton and P. R. Sanders (1984) *Plant Molecular Biology* 3, 371–378.
A. Frank., H. Guilley, G. Joward, K. Richards and L. Hirth (1980) *Cell* 21, 285–294.
R. C. Gardner et al, *Nucleic Acids Research* Vol. 9 No. 12: 287 (1981)
G. Guilley et al, *Cell* 30: 763 (1982)
T. Hohn et al, in Gene Cloning in Organisms Other than *E. coli*, p. 193, Hofschneider and Goebel, eds. (Springer Verlag, N.Y., 1982)
A. S. Howarth et al, *Virology* 112:678 (1981)
T. Maniatis et al, Molecular Cloning—A Laboratory Manual (Cold Spring Harbor, Lab, 1982)
R. E. F. Matthews (ed.) *Plant Virology* (Academic Press, N.Y., 1970).

R. C. Mulligan et al, *Nature* 277: 108 (1979).
R. N. Rao and S. Rogers, *Gene* 7: 79 (1979).
S. Rogers et al., (1985) *Plant Mol. Rep.* 3:111.
P. J. Southern & P. Berg, *J. Mol. Appl. Gen.* 1 327 (1982).
L. Stryer, *Biochemistry*, 2nd. ed. (Freeman and Co. San Francisco, 1981).
M. Zoller et al., (1982) *Nucleic Acids Res.* 10:6487.

We claim:

1. A method for transforming a plant cell which comprises transforming a plant cell with a chimeric DNA construct containing a promoter isolated from cauliflower mosaic virus (CaMV), said promoter selected from the group consisting of a CaMV(19S) promoter derived from the CaMV (19S) gene and a CaMV(35S) promoter derived from the CaMV(35S) gene, and a DNA sequence which is heterologous with respect to the promoter; wherein the promoter regulates the transcription of the DNA sequence.

2. The method of claim 1 in which the promoter is a CaMV(35S) promoter.

3. The method of claim 1 in which the promoter is a CaMV(19S) promoter.

4. The method of claim 1 in which the chimeric DNA construct comprises in the 5' to 3' direction:

(1) a CaMV(35S) promoter, (2) a DNA sequence encoding neomycin phosphotransferase II, and (3) a 3' non-translated polyadenylation sequence of nopaline synthase.

5. The method of claim 1 in which the chimeric DNA construct comprises in the 5' to 3' direction:

(1) a CaMV(19S) promoter, (2) a DNA sequence encoding neomycin phosphotransferase II, and (3) a 3' non-translated polyadenylation sequence of nopaline synthase.

6. The method of claim 1 in which the chimeric DNA construct is free of CaMV protein-encoding sequences.

* * * * *